United States Patent [19]
Kozaki et al.

[11] 4,369,177
[45] Jan. 18, 1983

[54] STABLE COMPOSITION OF S-ADENOSYL-L-METHIONINE

[75] Inventors: Yuichi Kozaki, Kakogawa; Shingo Hata, Takasago; Hajime Kawaharada, Kakogawa; Kiyoshi Watanabe, Akashi, all of Japan

[73] Assignee: Kanegafuchi Chemical Industry Company, Limited, Osaka, Japan

[21] Appl. No.: 208,842

[22] Filed: Nov. 20, 1980

[30] Foreign Application Priority Data

Dec. 4, 1979 [JP] Japan ........................ 54-157295
Jan. 10, 1980 [JP] Japan ........................ 55-1763

[51] Int. Cl.[3] ........................ A61K 31/70
[52] U.S. Cl. ........................ 424/175; 424/180; 536/27
[58] Field of Search ........................ 424/180, 127, 137, 147, 424/153, 154, 149, 175; 536/24, 26

[56] References Cited

U.S. PATENT DOCUMENTS 3,954,726 5/1976 Fiecchi ........................ 536/26
4,109,079 8/1978 Kawahara et al. ........................ 424/180
4,242,505 12/1980 Kawahara et al. ........................ 424/180

FOREIGN PATENT DOCUMENTS 2430999 1/1975 Fed. Rep. of Germany .
52-125194 10/1977 Japan .
54-154774 12/1979 Japan .
55-105700 8/1980 Japan .

*Primary Examiner*—Blondel Hazel
*Attorney, Agent, or Firm*—Armstrong, Nikaido, Marmelstein & Kubovcik

[57] ABSTRACT

A stable composition of S-adenosyl-L-methionine is disclosed which includes a salt of S-adenosyl-L-methionine and a pharmaceutically acceptable, water-soluble salt of a bivalent or trivalent metal. The salt of S-adenosyl-L-methionine is, for example, a salt of S-adenosyl-L-methionine with hydrochloric acid, sulfuric acid, p-toluenesulfonic acid, phosphoric acid, formic acid, acetic acid, citric acid, tartaric acid, or maleic acid; or a double salt of S-adenosyl-L-methionine with the foregoing acids. The salt of a bivalent or trivalent metal is, for example, calcium chloride, ferric chloride, magnesium chloride, or magnesium sulfate. A process for preparing the composition is also disclosed. The composition is suitable for preparing pharmaceutical preparations of S-adenosyl-L-methionine.

12 Claims, No Drawings

STABLE COMPOSITION OF S-ADENOSYL-L-METHIONINE

BRIEF SUMMARY OF THE INVENTION

The present invention relates to a stable composition of S-adenosyl-L-methionine (hereinafter referred to as SAM). More specifically, the present invention relates to a stable composition of SAM comprising a salt of SAM and a pharmaceutically acceptable, water-soluble salt of a bivalent or trivalent metal. The present invention also relates to a process for preparation of the SAM composition. The composition of the present invention provides a stable composition of SAM suitable for pharmaceutical uses.

It is known that SAM occurs widely in living organisms and acts as a methyl donor in many transmethylations in vivo. Pharmaceutical effects of SAM have been reported in various disorders such as adipohepatica, hyperlipemia, arteriosclerosis, depression, arthritis deformans, pains in some neurological manifestations, and sleeplessness.

Since SAM, as it is, is too unstable for pharmaceutical uses, many salts and compositions of SAM haven been proposed, for example, SAM.p-toluenesulfonate (German Pat. first publication No. 2336401, Japanese patent publication No. 35726/1977); a double salt of SAM with p-toluenesulfonic acid and sulfuric acid (German Pat. first publication) No. 2430999, Japanese patent publication No. 35727/1977); SAM.methanesulfonate, SAM.ethanesulfonate, SAM.dodecanesulfonate, SAM.1-octadecanesulfonate, SAM.2-chloroethanesulfonate, SAM.2-bromoethanesulfonate, SAM.2-oxyethanesulfonate, SAM.3-oxypropanesulfonate, SAM.d,l-10-camphorsulfonate, SAM.d,l-3-bromocamphorsulfonate, SAM.cystenate, SAM.benzenesulfonate, SAM.p-chlorobenzenesulfonate, SAM.2-mesitylbenzenesulfonate, SAM.4-biphenylsulfonate, SAM.1-naphthalenesulfonate, SAM.2-naphthalenesulfonate, SAM.5-sulfosalicylate, SAM.p-acetylbenzenesulfonate, SAM.1,2-ethanedisulfonate, SAM.o-benzenedisulfonate, SAM.-chondroitinsulfate, and a double salt of SAM with sulfuric acid and said sulfonic acids or chondroitinsulfate (German patent first publication No. 2530898, Japanese patent first publication No. 125717/1976; SAM.1,5-naphthalenesulfonate and SAM.1-amino-8-naphthol-2,4-disulfonate (Japanese patent first publication No. 38614/1978); SAM.citrate, SAM.tartrate, SAM.maleate, and SAM.ascorbate (French Pat. No. 2275220); a composition comprising SAM, sulfuric acid, and ribonucleotide-5'-monosulfate (Japanese patent first publication No. 109998/1979), a composition comprising SAM, sulfuric acid, and nucleotidesulfate (Japanese patent first publication No. 154774/1979); a composition comprising SAM, sulfuric acid, and a sulfate of monosaccharide or oligosaccharide (Japanese patent first publication No. 105700/1980); a composition comprising SAM, sulfuric acid, and cytidine-5'-monosulfate (Japanese patent first publication No. 28808/1979); a composition comprising SAM, sulfuric acid, and uridine-2'(3'),5'-disulfate (Japanese patent first publication No. 55598/1979; and a composition comprising SAM or its salt and a lithium salt (Japanese patent first publication No. 125194/1977).

Known SAM preparations, however, are not sufficiently stable at room temperature. Further, the acid content in them is high, so that their aqueous solutions are strongly acidic, the pH being 1-2 in a 50 mg/ml Sam aqueous solution. Therefore, on injection, the aqueous solutions must be neutralized for adjustment; on the other hand, their oral preparations are liable to exert harmful effects on digestive organs. Moreover, many known SAM preparations require complicated and costly procedures for their preparation.

Thus a sufficiently stable salt or composition of SAM which can be prepared economically and is suitable for pharmaceutical uses has practically not been known so far. Such a preparation of SAM has therefore been looked forward to.

The present inventors have undertaken various investigations in search of a stable composition of SAM which can be prepared economically and is suitable for pharmaceutical uses, and have completed the present invention.

The present invention is a stable composition of SAM and a process for preparation thereof. The composition comprises a salt of SAM and a pharmaceutically acceptable, water-soluble salt of a bivalent or trivalent metal. The salt of SAM in the composition of the present invention is a salt of SAM with an inorganic or organic acid. It also includes a double salt of SAM with inorganic or organic acids. Examples of the salt of SAM are those with hydrochloric acid, sulfuric acid, p-toluenesulfonic acid, phosphoric acid, formic acid, acetic acid, citric acid, tartaric acid, and maleic acid; and a double salt of SAM with the foregoing acids. The pharmaceutically acceptable, water-soluble salt of a bivalent or trivalent metal in the composition of the present invention includes, for example, calcium chloride, ferric chloride, magnesium chloride, and magnesium sulfate.

The process for preparation of the composition of the present invention comprises dissolving the salt of SAM described above and the salt of a bivalent or trivalent metal described above in an aqueous solvent to prepare an aqueous solution of the composition, then removing the aqueous solvent from the aqueous solution or adding an organic solvent to the aqueous solution to precipitate the composition.

According to the present invention, a composition of SAM which is stable for a long period of time even at a room temperature and which can be prepared easily at low cost is provided for pharmaceutical uses. In particular, oral preparations of SAM, such as a tablet, pill, and capsule, have come to be employed easily for medicinal uses thanks to the stable composition of the present invention.

DETAILED DESCRIPTION

The salt of SAM in the composition of the present invention can be obtained, for example, by the following known methods:

A. Preparation of SAM

1. SAM is produced in cells of microorganisms when the microorganisms are cultivated in a medium containing methionine [F. Schlenk et al., J. Biol. Chem., 229, 1051 (1957); F. Schlenk et al., Enzymologia, 29, 283 (1965)]. The microorganisms include, for example, those belonging to the genus Saccharomyces, Candida, Hansenula, Pichia, Cryptococcus, Rhodotorula, Trichosporon, Kloeckera, Torulopsis, Hanseniaspora, Sporobolomyces, Lipomyces, Tolula, Aspergillus, Penicillium, Mucor, and Rhizopus. Cells of a microorganism separated from the culture broth is extracted with an acid such as perchloric acid, hydrochloric acid, sulfuric acid, formic acid, and acetic acid; or an alkylformate to obtain an extract containing SAM.

The extract is applied to purification procedures hereinafter provided.

2. SAM is also synthesized enzymatically from adenosine triphosphate and methionine to obtain a solution containing SAM [S. Hervey Mudd et al., J. Biol. Chem., 231, 481(1958); Japanese patent publication No. 35727/1977]. The solution containing SAM is applied to the following purification procedures:

B. Purification of SAM

Isolation of SAM from the solutions containing SAM described above and purification thereof are carried out as follows: For example, any one of the following procedures or its proper combination can be employed. These procedures include, cation exchange chromatography; fractional precipitation with Reinecke's salt, picric acid, phosphotungstic acid, picrolonic acid, or methyl orange; activated charcoal adsorption chromatography; chelate resin chromatography; and fractional precipitation with polar organic solvents.

As described previously, the composition of the present invention comprises a salt of SAM and a pharmaceutically acceptable, water-soluble salt of a bivalent or trivalent metal. Examples of the salt of SAM and those of the pharmaceutically acceptable, water-soluble salt of a bivalent or trivalent metal are described hereinbefore.

The salt of SAM in the composition desirably consists of not less than 0.5 mole, preferably 0.5–3 moles, and more preferably 0.5–1 mole of the acid component and 1 mole of SAM component.

In the composition, the molar ratio of the metal salt of a bivalent or trivalent metal to SAM is desirably not less than 0.1, preferably 0.3–10, and more preferably 2–6.

An aqueous solution of the composition of the present invention desirably has a pH of 0.7–7, preferably 2–6, and more preferably 3–5.5 when the concentration of SAM in the aqueous solution is 50 mg/ml.

The composition of the present invention is stable especially in formulas prescribed above, in which the acid content can be varied in a wider range than is the case with known SAM preparations. In other words, it is to be noted that the composition of the present invention is stable even when the acid content is low or the pH of an aqueous solution of the composition is relatively high. On the contrary, in the case of most known SAM preparations, aqueous solutions thereof have a pH of about 1–2; therefore, when the preparations are used for injection, solutions thereof have to be neutralized to adjust their pH to that of body fluids, and when they are used orally, they are liable to exert harmful effects on digestive organs.

On the contrary, the SAM composition of the present invention suffers no such disadvantages in its medicinal applications both by injection and by oral administration.

In preparing the composition of the present invention, an aqueous solution containing the salt of SAM and the pharmaceutically acceptable, water-soluble salt of a bivalent or trivalent metal is prepared at first. The metal salt, examples of which are described previously, is dissolved in an aqueous solution containing the salt of SAM with stirring for a few minutes. Then the pH of the solution is adjusted, preferably, to the foregoing value described in connection with the pH of an aqueous solution of the composition, that is, a pH of 0.7–7, preferably 2–6, and more preferably 3–5.5 when the concentration of SAM in the aqueous solution is 50 mg/ml.

For the adjustment of the pH, an $OH^-$-type anion exchange resin or a metal hydroxide of which the metal, for example, corresponds to that of the bivalent or trivalent metal of the composition of the present invention is used. Cited as examples of the $OH^-$-type anion exchange resin are Amberlite IR-45 (a trademark of Rohm & Haas Co., U.S.A.), Dowex-1 (a trademark of The Dow Chemical Co., U.S.A.), and DIAION WA 10 (a trademerk of Mitsubishi Chemical Industries Ltd., Japan). Cited as examples of the metal hydroxide are calcium hydroxide, ferric hydroxide, and magnesium hydroxide.

If necessary, precipitates in the solution, if any, may be removed by filtration or centrifugation. The aqueous solution obtained above is then subjected to the following treatments. In one method, the aqueous solvent is removed from the aqueous solution, for example, by evaporation to dryness under reduced pressure or by lyophilization. The distillation or lyophilization is conducted at a temperature below 45° C., preferably below 35° C. As occasion demands, the composition thus obtained may be dried in vacuo over a desiccant such as phosphorus pentoxide, potassium hydroxide, and silica gel. A cold trap may also be used for the drying. Thus trace amounts of moisture in the composition can be removed.

In another method, an organic solvent is added to the aqueous solution described above to precipitate the composition. The organic solvent includes, for example, methanol, ethanol, isopropanol, n-propanol, n-butanol, sec-butanol, tert-butanol, acetone, methyl ethyl ketone, ethyl formate, methyl acetate, ethyl acetate, ethyl ether, 2-methoxyethanol, and dioxane. The resulting precipitate is separated from the liquid phase by filtration or centrifugation and dried under vacuum. As occasion demands, trace amounts of moisture can be removed by drying over a desiccant or by the use of a cold trap in the same manner as described above.

The composition obtained above is desirably dried until it contains 3% or less, preferably 1% or less, of moisture.

The composition of the present invention is stable for a long period of time even at a room temperature. The stability of the composition of the present invention was compared with that of two known SAM preparations, that is, SAM sulfate and a double salt of SAM with p-toluenesulfonic acid and sulfuric acid, as shown in examples hereinafter provided. The two known preparations are relatively stable at only strong acidity, whereas the composition of the present invention is stable at a wide range of acidity, that is, even at weak acidity. The composition of the present invention was more stable than the known two preparations when stored at a temperature of 40° C. for 3 months. Further, whereas known SAM preparations must be stored at a cool place, the composition of the present invention can be stored at a room temperature.

To further illustrate the present invention, but not by way of limitation, the following examples are given.

EXAMPLE 1

A SAM sulfate containing 2.2 molar ratio of sulfuric acid based on SAM was prepared by a known process [F. Schlenk et al., Enzymologia, 29, 283 (1965); Japanese patent publication No. 13680/1971]. In 100 ml of distilled water was dissolved 10 g of the SAM sulfate and the resulting aqueous solution, adjusted to pH 6 with Amberlite IR-45 [OH$^-$-type], was filtered to obtain 90 ml of an aqueous solution of SAM.

In the aqueous solution of SAM were each dissolved various quantities of calcium chloride, ferric chloride, magnesium chloride, and magnesium sulfate to prepare respective aqueous solutions containing examples of two components of the composition of the present invention, namely, a salt of SAM and a salt of a bivalent or trivalent metal. The aqueous solutions were each diluted to a concentration of 50 mg/ml of SAM with distilled water and adjusted to the pH of 1.2, 3, 4, and 5 with 6 N sulfuric acid.

The pH-adjusted aqueous solutions were each centrifuged at 3000 r.p.m. for 10 min to remove resulting precipitates. The supernatant (1 ml) were each pipetted into 3 ml-glass ampules and lyophilized at a temperature of 40° C. or less for 16 hr under 0.05 Torr to prepare compositions. The samples, sealed by a gas burner, were each stored at a temperature of 40° C. and at 75% humidity for 3 months for a stability test. Results of the stability test are tabulated in Table 1.

In place of lyophilization, evaporation to dryness under reduced pressure can also be applied in the foregoing process.

As an explanation of the process, it may be added that, when the composition is prepared by removing the aqueous solvent from the aqueous solution of components of the composition as is the case with this example, the ratio of the components in the composition is determined when the components are dissolved in an aqueous solution.

TABLE 1

Stability Tests of the Composition of the Present Invention and Known SAM Preparations

| Composition of the present Invention | | pH adjusted at the time of the preparation | | | | | | | |
|---|---|---|---|---|---|---|---|---|---|
| | Molar ratio of metal salts | 1.2 | | 3 | | 4 | | 5 | |
| Metal salt | based on SAM in the composition | A (%) | B | A (%) | B | A (%) | B | A (%) | B |
| Calcium chloride | 2 | 88.3 | 2.4 | 86.3 | 1.1 | 94.2 | 0.8 | 94.5 | 0.6 |
| | 4 | 93.1 | 2.4 | 90.8 | 1.1 | 97.6 | 0.8 | 94.8 | 0.6 |
| | 6 | 92.8 | 2.4 | 88.4 | 1.1 | 98.5 | 0.8 | 97.3 | 0.6 |
| Ferric chloride | 1 | 87.5 | 2.1 | 88.7 | 0.9 | 93.1 | 0.6 | 90.5 | 0.5 |
| | 2 | 90.0 | 2.0 | 89.4 | 0.9 | 94.9 | 0.5 | 91.1 | 0.5 |
| | 4 | 91.6 | 1.9 | 90.7 | 0.8 | 93.4 | 0.5 | 91.4 | 0.4 |
| Magnesium chloride | 2 | 92.0 | 2.3 | 94.6 | 1.0 | 97.8 | 0.75 | 98.2 | 0.6 |
| | 4 | 94.5 | 2.3 | 97.1 | 1.0 | 98.3 | 0.75 | 98.0 | 0.6 |
| | 6 | 93.7 | 2.3 | 95.5 | 1.0 | 98.0 | 0.75 | 97.4 | 0.6 |
| Magnesium sulfate | 2 | 90.4 | 2.4 | 90.6 | 1.1 | 94.4 | 0.8 | 96.4 | 0.6 |
| | 4 | 93.9 | 2.4 | 96.3 | 1.1 | 97.6 | 0.8 | 97.2 | 0.6 |
| | 6 | 93.1 | 2.4 | 96.7 | 1.1 | 98.1 | 0.8 | 98.8 | 0.6 |
| Known SAM preparation | | | | | | | | | |
| SAM · sulfate | | 36.1 | 2.3 | 17.5 | 1.0 | 11.2 | 0.75 | 10.5 | 0.6 |
| a double salt of SAM with p-toluenesulfonic acid and sulfuric acid | | 87.4 | 2.5 | 37.0 | 1.2 | 34.5 | 1.0 | 33.4 | 0.8 |

(note)
A: remaining SAM
B: the molar ratio of the acid component to SAM in the preparation As can be seen from Table 1, the composition of the present invention is more stable than known SAM sulfate and a double salt of SAM with p-toluenesulfonic acid and sulfuric acid. This difference is particularly conspicuous at pH 3-5.

EXAMPLE 2

SAM chloride was prepared in the same manner as in Example 1 with the exception that hydrochloric acid was used in place of sulfuric acid.

In 60 ml of distilled water was dissolved 6 g of SAM chloride. Three grams each of calcium chloride, ferric chloride, magnesium chloride, and magnesium sulfate was each dissolved in 15 ml of the aqueous solution containing SAM. The resulting aqueous solutions containing two components of the composition of the present invention were each filtered to remove insoluble materials. Acetone (30 ml) was added to the each filtrate to precipitate the each composition. The resulting precipitates were each washed with acetone and dried overnight over phosphorus pentoxide to afford compositions of the present invention.

The compositions were each placed in 10 ml-glass vials and the vials were each sealed with rubber caps. The vials were each stored at a temperature of 40° C. and at 75% humidity for 3 months for a stability test. Results of the stability test are tabulated in Table 2.

As an explanation of the process, it may be added that, when the composition is prepared by adding an organic solvent to an aqueous solution of components of the composition, the ratio between components is variable according to the kind and quantity of the organic solvent added.

An addition of the minimum quantity of an organic solvent to the aqueous solution gives rise to the composition in which the molar ratio of the metal salt and the acid component to SAM is high. On the other hand, when larger quantities of an organic solvent are added to the aqueous solution, the resulting composition has the low ratio of said components to SAM.

TABLE 2

Stability Tests of the Composition of the Present Invention and Known SAM Preparations

| Metal salt | Molar ratio of metal salts based on SAM in the preparation | Molar ratio of the acid component based on SAM in the preparation | Remaining SAM (%) |
|---|---|---|---|
| Composition of the Present Invention | | | |
| Calcium chloride | 3.5 | 1.0 | 98.2 |
| Ferric chloride | 4.0 | 1.0 | 95.4 |
| Magnesium chloride | 3.8 | 1.0 | 97.9 |
| Magnesium sulfate | 4.2 | 1.0 | 97.4 |
| Known SAM Preparation | | | |
| SAM · sulfate | — | 2.5 | 46.3 |
| a double salt of SAM with p-toluenesulfonic acid and sulfuric acid | — | 3.1 | 90.1 |

As can be seen from Table 2, the composition of the present invention, even when the acid content therin is low, is more stable than known SAM preparations, namely, SAM.sulfate and a double salt of SAM with p-toluenesulfonic acid and sulfuric acid in the most stable state in which the acid content is high.

What is claimed is:

1. A stable composition of S-adenosyl-L-methionine which comprises a salt of S-adenosyl-L-methionine and a pharmaceutically acceptable, water-soluble salt of a bivalent or trivalent metal wherein said composition is an aqueous solution.

2. The composition according to claim 1 wherein the salt of a bivalent or trivalent metal is a member selected from the group consisting of calcium chloride, ferric chloride, magnesium chloride, and magnesium sulfate.

3. The composition according to claim 1 wherein the salt of S-adenosyl-L-methionine is a member selected from the group consisting of salts of S-adenosyl-L-methionine with hydrochloric acid, sulfuric acid, p-toluenesulfonic acid, phosphoric acid, formic acid, acetic acid, citric acid, tartaric acid, and maleic acid; and a double salt of S-adenosyl-L-methionine with said acids.

4. The composition according to claim 1, claim 2, or claim 3 wherein the salt of S-adenosyl-L-methionine consists of not less than 0.5 mole of the acid component and 1 mole of the S-adenosyl-L-methionine component.

5. The composition according to claim 4 wherein the salt of S-adenosyl-L-methionine consists of 0.5–3 moles of the acid component and 1 mole of the S-adenosyl-L-methionine component.

6. The composition according to claim 4 wherein the salt of S-adenosyl-L-methionine consists of 0.5 to 1 mole of the acid component and 1 mole of the S-adenosyl-L-methionine component.

7. The composition according to claim 1, claim 2, or claim 3 wherein the molar ratio of the salt of a bivalent or trivalent metal to S-adenosyl-L-methionine is not less than 0.1.

8. The composition according to claim 7 wherein the molar ratio of the metal salt of a bivalent or trivalent metal to S-adenosyl-L-methionine is 0.3 to 10.

9. The composition according to claim 7 wherein the molar ratio of the metal salt of a bivalent or trivalent metal to S-adenosyl-L-methionine is 2 to 6.

10. The composition according to claim 1, claim 2, or claim 3 of which the aqueous solution has a pH of 0.7–7 when the concentration of S-adenosyl-L-methionine in the aqueous solution is 50 mg/ml.

11. The composition according to claim 10 of which the aqueous solution has a pH of 2–6 when the concentration of S-adenosyl-L-methionine in the aqueous solution is 50 mg/ml.

12. The composition according to claim 10 of which the aqueous solution has a pH of 3–5.5 when the concentration of S-adenosyl-L-methionine in the aqueous solution is 50 mg/ml.

* * * * *